United States Patent [19]
Davis et al.

[11] 4,411,648
[45] Oct. 25, 1983

[54] IONTOPHORETIC CATHETER DEVICE

[75] Inventors: Charles P. Davis; Michael M. Warren, both of Galveston, Tex.; David W. Arnett, Monrovia, Calif.

[73] Assignee: Board of Regents, The University of Texas System, Austin, Tex.

[21] Appl. No.: 272,484

[22] Filed: Jun. 11, 1981

[51] Int. Cl.³ .............................................. A61H 1/30
[52] U.S. Cl. ...................................................... 604/21
[58] Field of Search ...................... 128/207.21, 207.22, 128/348–350, 784–786, 362; 604/20, 21

[56] References Cited

U.S. PATENT DOCUMENTS

| | | | |
|---|---|---|---|
| 2,121,875 | 6/1938 | Kruse et al. | 128/362 X |
| 3,122,137 | 2/1964 | Erlanger | 128/172.1 |
| 3,163,166 | 12/1964 | Brant et al. | 128/405 |
| 3,326,213 | 6/1967 | Gallagher | 128/156 |
| 3,716,054 | 2/1973 | Porter et al. | 128/172.1 |
| 3,964,477 | 6/1976 | Ellis et al. | 128/172.1 |
| 4,027,393 | 6/1977 | Ellis et al. | 32/10 |
| 4,054,139 | 10/1977 | Crossley | 128/260 |
| 4,314,554 | 2/1982 | Greatbatch | 128/207.21 |

FOREIGN PATENT DOCUMENTS 2720776  11/1978  Fed. Rep. of Germany ... 128/349 R

OTHER PUBLICATIONS

Akiyama et al., *Journal of Urology*, vol. 121: pp. 40–42 (1979).
Berger et al., *Antimicrobial Agents and Chemotherapy*, vol. 9: pp. 357–358 (1976).
Spadaro, *Antimicrobial Agents and Chemotherapy*, vol. 6: pp. 637–642 (1974).

*Primary Examiner*—Lee S. Cohen
*Attorney, Agent, or Firm*—Arnold, White & Durkee

[57] ABSTRACT

A urinary catheter which comprises two internal heavy metal-containing electrodes disposed proximate the distal orifice of the catheter. The catheter is adapted for iontophoresis application for the purpose of preventing bacterial infection associated with catheterization procedures. Provision is made for connecting the electrodes to a constant electromotive force source. Iontophoretic operation of the catheter employs electromotive force to generate heavy metal ions at the electrode surfaces. The heavy metal ions are driven into an electrolyte solution provided by urine or tissue fluid near the site of the catheter tip. Heavy metal ions such as gold, silver, platinum, iron, and copper have been demonstrated to have antibacterial activity.

10 Claims, 3 Drawing Figures

IONTOPHORETIC CATHETER DEVICE

BACKGROUND OF THE INVENTION

The present invention relates to medical instrumentation; and more particularly to iontophoretic catheter apparatus and application for the sterilization of a fluid path.

It has been estimated that approximately ten to fifteen percent of hospitalized patients are subject to indwelling urinary catheterization. Of these catheterized patients, about twenty-five percent contract bacterial infections of the urinary tract.

The insertion of a catheter through the urethra into the bladder often contaminates the normally sterile internal duct environment. As a catheter is introduced through the urethra passageway or a surgically created opening to the bladder, bacteria normally found on the skin surface are introduced onto the catheter surfaces. As the catheter progresses through the urethra or opening, a bacterial inoculum is carried along to the normally sterile sites. The bacteria then colonize and eventually spread to regions uncontacted by the catheter.

Accordingly, it is recognized by physicians that catheterization presents a risk of bacterial induced cystitis or pyelonephritis and that risk increases proportionally with the period of catheterization time.

Various methods and treatments have been employed in an effort to reduce the possibility of bacterial infection associated with catheterization. Most commonly, physicians have sought to avoid infection by limiting the time of catheterization, by increasing water intake to increase voiding, by designing catheter systems closed to external contaminants, by preventing urine from flowing retrograde into the bladder, and by frequently exchanging used catheters for new ones. Further, antibiotics have been applied both prophylactically and remedially to reduce the occurrence of bacterial infection associated with catheterization.

Specifically, topical antibiotics such as neomycin, bacitracin, and polymyxin B sulfate are applied to the catheter surfaces prior to catheter insertion. The intent of this treatment is to prevent subsequent infection by the bacteria initially carried along the catheter surface as it progresses through the urethra. Although such antibiotic treatment is often effective in preventing initial contamination, if the catheter remains in place for an extended period of time systemic reapplication of the antibiotic is necessary to maintain prophylaxis.

Recently it has been suggested that silver plated catheters help prevent urinary tract infections through a process called oligodynamics. Heavy metals, in particular, gold, silver and copper, exert in the form of metal ions a profound bacterial effect, the so-called oligodynamic activity. Such material is effective in very small quantities and effective over long periods of time to inhibit the growth of bacteria. For example, U.S. Pat. No. 4,054,139 describes an oligodynamic catheter which comprises an internal and external immobile surface coating of silver onto a catheter. According to the invention, small quantities of silver exposed as part of the catheter surface are effective in avoiding infection of surrounding tissues contacting the catheter surface. Because of the limited diffusion of silver ions from the silver coating, the antibacterial effect, however, is primarily a site-specific surface effect.

Although some of the prior art solutions have been successful under certain conditions, the need remains for other practical and inexpensive solutions to the problem of catheterization associated bacterial infection. Especially, the need remains for a catheter device which is effective in killing bacteria suspended in a fluid phase over an extended period of time.

SUMMARY OF THE INVENTION

In accordance with the present invention, a method and apparatus is provided for preventing bacterial infection associated with catheterization procedures.

It is, therefore, a feature of the present invention to provide an inexpensive, compact and simple to use catheter device which is effective in preventing catheter associated bacterial infection during the entire course of catheterization.

Further, it is a feature in the practice of the present invention to generate heavy metal ions such as gold, silver, platinum, iron, or copper to prevent bacterial growth in the fluid phase contacting the catheter surfaces.

Another feature of the present invention is to provide continuous, effective antibacterial activity without administration of antibiotics or frequent catheter exchanges.

These and other objects which would be apparent to those skilled in the art after reading this specification, have been achieved by providing a catheter construction adapted for iontophoretic application. Iontophoresis is the process of electrochemically generating metallic ions at an electrode surface which are subsequently driven into the surrounding tissue or fluid path by the influence of the electromotive force.

The metal specific electrochemical products from the electrode interface exert antibacterial action upon contact and interaction with bacteria present near the vicinity of the electrodes.

The disclosed preferred iontophoretic apparatus includes a standard urinary catheter comprising an elongated tubular member having included internally two heavy metal-containing electrodes disposed proximate the distal orifice of the catheter. Connection means are provided to couple the electrodes to a constant current source.

In the application of the disclosed invention, the catheter with associated electrodes is inserted through a patient's urethra. Once the catheter is in place, the electrodes are coupled to the constant current source. A complete circuit is provided between the electrodes by the urine fluid flowing through the orifice. The urine which contains salts serves as an electrolyte path. Electromotive force from the source is sufficient to ionize the metallic matter from the electrodes to such a concentration to effect bactericidal and bacteriostatic action. Heavy metal ion concentrations as low as $10^{-6}$M have been shown to effect antibacterial action.

BRIEF DESCRIPTION OF THE DRAWINGS

A more complete appreciation of the invention may be had by reference to the accompanying drawings, illustrating a preferred embodiment of the invention to be described in detail, wherein.

DETAILED DESCRIPTION OF THE PREFERRED EMBODIMENTS

Figure 1:
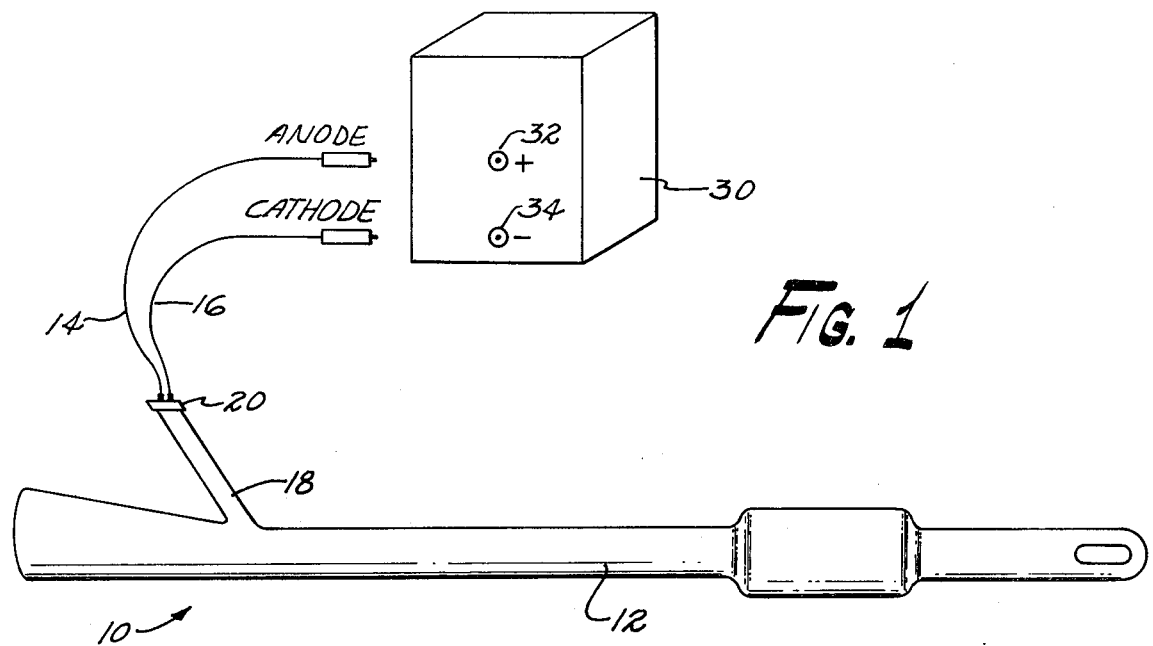
FIG. 1 is an illustration of the urinary catheter ready for use.

Referring to the drawings, and particularly to FIG. 1, there is shown an overall view of preferred embodiment of an iontophoretic cathether of the present invention. The illustrated iontophoretic catheter is generally indicated by reference numeral 10. Iontophoretic catheter 10 comprises a urinary catheter 12, having an elongated tubular member adapted for passage through the length of a patient's urethra to the bladder terminus. The urinary catheter may desirably be one of several indwelling urinary catheters presently on the market. For example, urinary catheter 12 may desirably be a FOLEY catheter. Further included are electrodes originating at the proximal end of urinary catheter 12 at port 18 and running along the internal length of the catheter lumen to the distal end. Port 18 is adapted with a connector 20 which provides a conductive electrical contact between the internal electrodes and external leads 14 and 16.

Iontophoretic catheter 10 further is adapted to accommodate current from a constant current source 30. Constant current source 30 is adapted to accept external leads 14 and 16 which transmit current to the internal electrodes. The constant current source is desirably a variable adjustable current source supplying between 1 and 1000 microamps.

Figure 2:
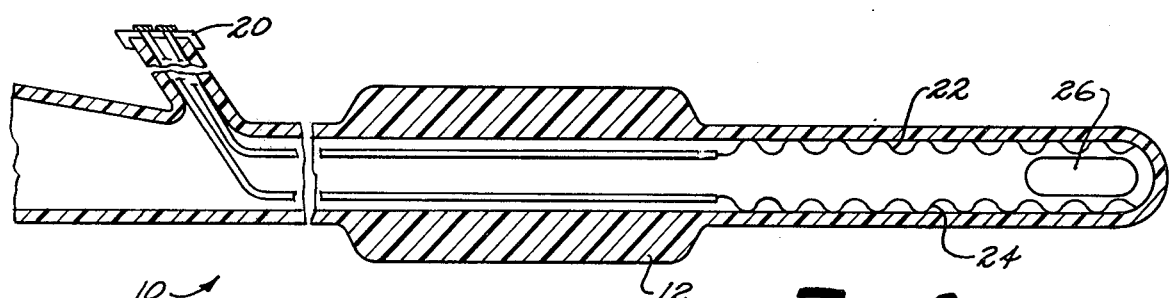
FIG. 2 is a cross-sectional view of the catheter.

As shown in FIG. 2, electrodes 22 and 24 extend the length of the inner catheter lumen. Electrodes 22 and 24 may desirably be electrode wires passed through the lumen, and terminating at the distal end of the catheter lumen. Care must be taken that the electrodes 22 and 24 do not contact each other, otherwise a short develops when a current is passed through the wires. Accordingly, the electrodes are insulated for a distance along the lumen. Suitably at the distal end near the collection orifice 26, the electrodes 22 and 24 are exposed to the inner catheter lumen. It is preferred that the electrodes provide an exposed operational surface near the collection orifice, such that iontophoresis is practiced at the site most likely to be contaminated with a bacterial inoculum.

In one aspect of the invention, the electrodes extend the length of the catheter embodied within the catheter tubular wall. Such a construction provides insulation to the electrodes, since the catheter walls are desirably constructed of non-conducting materials. Further, this particular construction insures the electrodes will not become tangled or snarled within the catheter lumen and subsequently block fluid flow during operation. Near the orifice the electrodes exit the tubular wall exposing surface to the inner lumen.

Alternatively, the electrodes may extend uninsulated along the entire inner catheter lumen to maximize the effective sterilization volume. In such a construction, the electrodes are desirably embedded or imprinted along the inner catheter tubular wall to maintain separation from each other.

Exposed electrodes 22 and 24 are displaced on either side of collection orifice 26. This placement of the electrodes prevents occlusion of the orifice and prevents electrode penetration outside the inner catheter lumen. Further, displacement of the electrodes immediately away from the orifice prevents electrode contact to surrounding tissue when the catheter is in use.

In the operation of the present invention, electrode 22 is designated the positive electrode or anode. Positive electrode 22 is preferably a gold wire, gold-plated electrode or gold-salt electrode. Other electrodes containing heavy metals such as silver, platinum, copper or stainless steel may also be used in the construction of positive electrode 22. These materials, however, do not provide optimum bactericidal effects at currents which have no significant effect on surrounding tissues.

Electrode 24 provides a return path for current conduction to the constant current source. Accordingly, electrode 24 is the cathode or negative electrode. Negative electrode 24 may be constructed of any electron conducting material, including but not limited to gold, silver, platinum, copper, stainless steel, or nickel. In a preferred embodiment of the invention, both electrodes 22 and 24 are gold containing electrodes. According to such a construction wherein each electrode is gold containing, there need not be a specific designation as to which is the anode or cathode. Electrode polarity connections to the constant current source are interchangeable when each electrode is constructed of the same material.

Electrodes 22 and 24 originate at port 18. Port 18 is further adapted with a connector 20. Connector 20 provides a conductive contact for electrodes 22 and 24. Further, connector 20 provides a seal for port 18. Such a seal is desirable to maintain sterility of the catheter during storage, prevent contamination of the electrodes and inner catheter shaft during operation, and prevent leakage of urinary fluid during the drainage operation.

Connection 20 further provides means for detachably coupling external leads 14 and 16 in electrical conductive contact with electrodes 22 and 24 respectively. Accordingly, lead 14 when coupled relative to electrode 22 is the anode lead. Similarly, lead 16 in conductive contact with electrode 24 is the cathode lead.

In accordance with the practice of the disclosed invention, urinary catheter 12 with associated electrodes is provided as a disposable iontophoretic unit for one time application to a patient. Such catheters are provided sterile prior to patient insertion. Prior to use, the distal end of outer catheter tubular wall is suitably lubricated with a water soluble jelly. Moreover, the distal end and other catheter wall may be coated with an antibiotic ointment as an additional prophylaxis against bacterial infection. Passage of the catheter tube through the length of a patient's urethra to bladder terminus is performed in the customary manner.

Once the urinary catheter is in place, external leads 14 and 16 are coupled to the connector 20. Further, external leads 14 and 16 are coupled respectively to the positive and negative terminals provided by constant current source 30.

In the preferred embodiment constant current source 30 provides a low intensity direct current to anode electrode 22 via anode lead 14. The constant current source is capable of supplying enough current to ionize the selected electrode metal to an effective concentration for antibacterial action. It is preferred that the constant electromotive force source have capacity for variable amperage output, desirable between 10 and 1000 microamps. The desirable electromotive force when employing gold electrodes for antibacterial effect is in the range of 10 microamps to 500 microamps. The optimum current for the present invention employing gold electrodes is 400 microamps. This electromotive force has been determined to ionize gold to such a concentration lethal to bacterial cells but to have no significant deleterious effect on surrounding tissue.

In the operation of the iontophoretic catheter a complete current circuit is provided from the anode to cathode through the urine fluid which is collected through orifice 26. This urine fluid provides an electrolyte path for the generated gold ions at the anode electrode 22. The generated cations migrate from the anode to the cathode provided by electrode 24, thereby completing the electrical circuit back to the negative terminal of source 30.

Without wishing to be limited to the theory of the invention, it is believed the bactericidal effect of the present invention is a consequence of bacterial complexation with the heavy metal cations, particularly gold cations as the preferred cation, generated at the anode and subsequent interference with the genetic replication of the bacteria.

Figure 3:
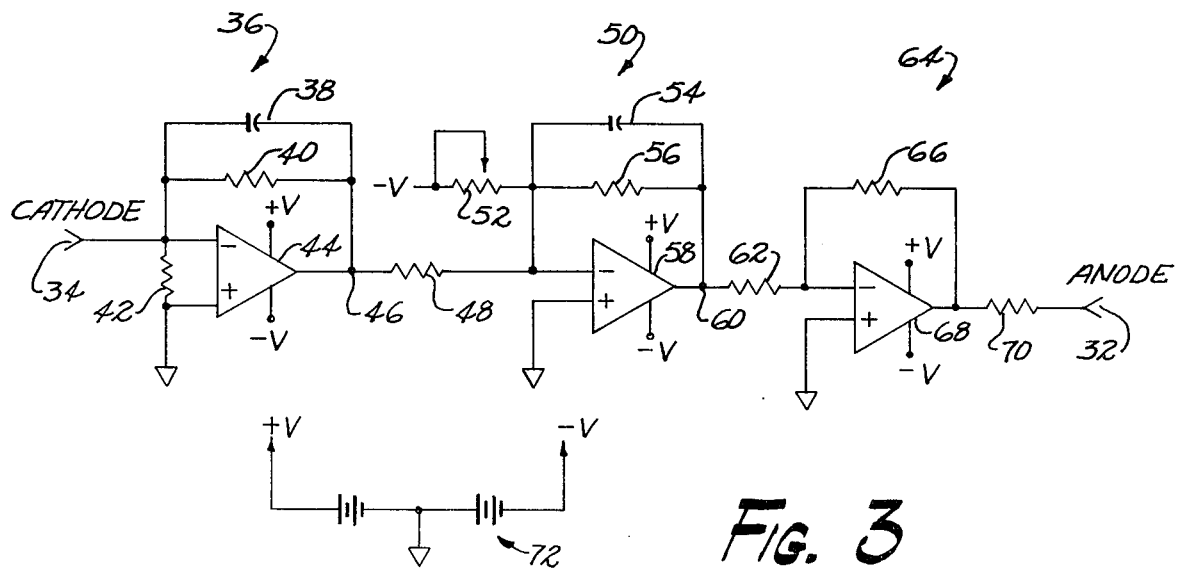
FIG. 3 is a schematic illustrating a suitable constant current source for the electrodes.

Referring next to FIG. 3, there is depicted a schematic for a preferred constant current source 30. In accordance with an implementation of the preferred embodiment, FIG. 3 depicts a circuit which serves to maintain the flow of current between the cathode and anode of the catheter illustrated in FIG. 1 at a constant preset value. Basically, the constant current source 30 utilizes three sub-functional units: a current to voltage converter 36, a voltage comparator 50, and a voltage to current converter 64. Each of these sub-functional units comprises operational amplifiers and associated components such as resistors and capacitors.

The current to voltage converter 36 comprises an operational amplifier 44, in the preferred embodiment typically a TL082 manufactured by Texas Instruments, Inc., Dallas, Tex., with inverting input connected to cathode terminal node 34, non-inverting input connected to ground, and output connected to node 46; bias stabilization resistor 42, typically 100 kilo ohms, connected between node 34 and ground; feedback capacitor 38, typically 0.1 micro farads, connected between nodes 34 and 46; and feedback resistor 40, typically 1 kilo ohm connected between 34 and 46. The input to the current to voltage converter is through cathode terminal node 34. The input current flows into the feedback resistor 40 to node 46. Operational amplifier 44 maintains the voltage at node 46 equal to the input current in amperes multiplied by the resistance of feedback resistor 40 in ohms. This node voltage is applied as the input to the next sub-function, the voltage comparator 50.

The voltage comparator 50 comprises an operational amplifier 58, typically a TL082, with non-inverting input connected to ground, and output connected to node 60; an input resistor 48, typically 10 kilo ohms, connected between node 46 and the inverting input of op-amp 58; potentiometer 52, typically 500 kilo ohms, with slider terminal and one end terminal connected to the positive supply voltage node (+v) and the other end terminal connected to op-amp 58 inverting input; feedback capacitor 54, typically 0.01 micro farads, connected between node 60 and operational amplifier 58 inverting input; feedback capacitor 54, typically 0.01 micro farads, connected between node 60 and operational amplifier 58 inverting input; and feedback resistor 56, typically 100 kilo ohms, connected in parallel with capacitor 54. This comparator produces an output which is proportional to the algebraic sum of the currents flowing from node 46 through resistor 48 and from +v through potentiometer 52, into the inverting input node of op-amp 58, and then through resistor 56 to output node 60. Since one of these currents is adjustable by means of potentiometer 52, while the other is proportional to the cathode input current, the output voltage of this comparator can be adjusted to a desired value over a range of input currents. This output voltage is applied as the input to the final sub-function, the voltage to current convertor.

The voltage to current converter 64 comprises an operational amplifier 68, typically a 3140 manufactured by RCA Corporation, Somerville, N.J., with non-inverting input connected to ground; input resistor 62, typically 10 kilo ohms, connected between op-amp 68 inverting input and node 60; feedback resistor 66, typically 100 kilo ohms, connected between the output and inverting input of op-amp 68; and output and inverting input of op-amp 68; and output resistor 70, typically 10 kilo ohms, connected between the output terminal of op-amp 68 and anode terminal node 32. The input current flows through resistors 62 and 66 to the output of op-amp 68. The op-amp establishes an output voltage at its output node that is proportional to the voltage at node 60, and therefore proportional to the difference between the cathode input current and the preset value established by potentiometer 52. This output voltage establishes a current through resistor 70 to the anode terminal node 32. Since this current flows through the electrodes of the catheter and the electrolyte in which the catheter is placed, the current through this electrolyte is selectable through setting potentiometer 52. Once a setting has been established, the circuit will maintain that level of current over a wide range of electrolyte conductivities.

The overall circuit will, therefore, sense the amount of cathode current; compare this current with a predetermined value; and adjust the anode current causing the current through the connected catheter to be maintained at a predetermined value. Any change in anode-cathode conductivity is compensated by re-adjusting the anode-cathode current automatically.

ILLUSTRATIVE EXAMPLE OF THE INVENTION

A catheter comprising two internally placed gold wire electrodes was coupled with a battery operated constant current source. The iontophoretic catheter device was immersed into a liquid culture media which had previously been inoculated with $10^8$ *Escherichia coli* bacteria. The media and catheter were incubated at 37° C. for 24 hours. During this period a current of 400 microamps was conducted through the catheter electrodes to effect iontophoresis. After 24 hours of current flow, culture samples were taken and evaluated for bacterial viability. No viable organisms were found in those vials subjected to iontophoresis. Control vials inoculated with bacteria not subjected to iontophoresis exhibited bacterial proliferation.

The foregoing description of the invention has been directed to a particular preferred embodiment for purposes of explanation and illustration. Although the iontophoretic catheter of the present invention is particularly suitable for preventing infection associated with urinary catheterization, catheters adapted for physiological use such as those catheters for wound drainage, catheters of the arterial, venous, intraperitoneal and cannual types, shunts to internal organs, and intracranial pressure monitoring devices such as Richmond bolt assembly may be adapted as described herein to maintain sterility of a surrounding fluid path. Furthermore, the catheters of the present invention could be useful in veterinary medicine for similar purposes.

Similarly, the constant source depicted herein may be substituted with other means serving to provide a constant electromotive force input to the cathode electrodes. For example, alternating current adapted with a direct current convertor may suitably be employed to generate an electromotive force supply to the electrodes. Accordingly, it is to be understood that the present invention admits to other embodiments and employment in other applications without departing from the teachings of the invention as defined in the following claims.

What is claimed is:

1. Apparatus adapted for iontophoresis application to provide antibacterial activity which comprises:
    a catheter adapted for physiological use comprising an elongated tubular member having an orifice at the distal end for the passage of electrolyte fluid therethrough;
    a positive electrode containing a heavy metal, the positive electrode disposed and terminating internally to the tubular member, and having a surface exposed to the lumen of the tubular member proximate the orifice;
    a negative electrode disposed and terminating internally to the tubular member, the negative electrode having a surface exposed to the lumen of the tubular member proximate the orifice; and
    means for conductive electrical connection to a constant current source from each of the said positive and negative electrodes.

2. The apparatus of claim 1 wherein the heavy metal of the positive electrode is selected from the group consisting of gold, silver, platinum, iron, copper and salts thereof.

3. The apparatus of claim 1 wherein the positive electrode comprises gold or gold salts.

4. The apparatus of claim 1 wherein both the positive and negative electrodes comprise gold or gold salts.

5. A method for preventing bacterial infection associated with catheterization the method comprising:
    inserting into a physiological fluid passageway a catheter having internally disposed and terminating therein a heavy metal containing positive electrode and a heavy metal containing negative electrode;
    connecting the positive electrode to the positive terminal of a constant current source;
    connecting the negative electrode to the negative terminal of a constant current source;
    providing an electromotive force flow through the positive electrode to produce heavy metal ions at a sufficient concentration to inhibit proliferation of bacteria.

6. The method according to claim 5 wherein the electromotive force flow is in the approximate range of 40 microamps to 500 microamps.

7. The method according to claim 5 wherein the positive electrode comprises gold or gold salts.

8. The method according to claim 7 wherein electromotive force flow is approximately 400 microamps.

9. The method according to claim 5 wherein the positive and negative electrodes comprise gold or gold salts.

10. The method according to claim 5 wherein the catheter is inserted through the urethra of a patient to accomplish urinary catheterization.

* * * * *